United States Patent [19]

Borody

[11] Patent Number: 5,519,014
[45] Date of Patent: May 21, 1996

[54] TREATMENT OF NON-INFLAMMATORY AND NON-INFECTIOUS BOWEL DISORDERS

[76] Inventor: Thomas J. Borody, 144 Great North Road, Five Dock NSW 2046, Australia

[21] Appl. No.: 261,874

[22] Filed: Jun. 17, 1994

Related U.S. Application Data

[63] Continuation of Ser. No. 30,281, filed as PCT/AU91/00482, Oct. 17, 1991, published as WO92/06690, Apr. 30, 1992.

[30] Foreign Application Priority Data

Oct. 22, 1990 [AU] Australia ............... PK 2950

[51] Int. Cl.$^6$ .................. A61K 31/60; A61K 31/615
[52] U.S. Cl. .............................. 514/159; 514/166
[58] Field of Search ..................... 514/154, 166, 514/159

[56] References Cited

FOREIGN PATENT DOCUMENTS 2021409  12/1979  United Kingdom ............. 514/159

OTHER PUBLICATIONS

Chem. Abst. 104–39741H (1986).
Chem. Abst. 115–85417G (1991).
Chem. Abst. 116–201087W (1992).
Diseases of the Colon and rectum vol. 27, No. 8, 1984, pp. 513–514.
Gastroenterology vol. 94, No. 5, May 1988, p. A426.

*Primary Examiner*—Jerome D. Goldberg
*Attorney, Agent, or Firm*—James Ray & Associates

[57] ABSTRACT

A medicine for treating non-inflammatory and non-infectious bowel disorders, such as irritable bowel syndrome, constipation, non-ulcer dyspepsia, gastro-oesophageal reflux with or without oesophagitis, and diverticular disease, comprising a salicylic acid derivative, such as any one of sulfasalazine, 5-aminosalicylic acid, 4-aminosalicylic acid, and benzalazine, or a combination of any two or more thereof. The treatment of those disorders comprises taking the medicine by mouth to provide a dosage rate of the salicylic acid derivative of from 200 mg to 18 g per day.

12 Claims, 2 Drawing Sheets

PATIENT CHARACTERISTICS

| NO. | AGE | SEX | PAIN | BLOAT-ING | DIAR-RHEA | CONSTI-PATION | FLATU-LENCE | DURA-TION YRS. |
|---|---|---|---|---|---|---|---|---|
| | | | | SYMPTOM SEVERITY SCORES AT ENTRY | | | | |
| 1 | 36 | F | 5 | 6 | – | 7 | – | 6 |
| 2 | 33 | F | 7 | – | – | 7 | – | 5 |
| 3 | 26 | F | 4 | 6 | – | 7 | – | 5 |
| 4 | 60 | F | 7 | 4 | 6 | – | 3 | 15 |
| 5 | 42 | F | 7 | – | 6 | 6 | 4 | 9 |
| 6 | 33 | F | 7 | 4 | 6 | 7 | – | 5 |
| 7 | 37 | F | – | – | 8 | – | 3 | 6 |
| 8 | 30 | F | 6 | – | 6 | – | – | 10 |
| 9 | 48 | F | 7 | – | – | 7 | 3 | 15 |
| 10 | 38 | F | 6 | 8 | 8 | – | 6 | 7 |
| 11 | 44 | F | 8 | 7 | 7 | – | – | 6 |
| 12 | 45 | F | 3 | 4 | 9 | – | – | 10 |
| 13 | 39 | F | 2 | 4 | 9 | – | 3 | 7 |
| 14 | 24 | F | | 3 | 6 | 5 | – | 3 |
| 15 | 56 | F | 6 | 4 | 7 | – | 3 | 15 |
| 16 | 37 | M | 5 | – | 7 | – | 5 | 7 |
| 17 | 45 | M | 6 | – | 9 | – | – | 10 |
| 18 | 36 | M | 8 | – | 6 | – | – | 5 |
| 19 | 59 | M | 7 | 3 | – | 7 | 3 | 15 |
| 20 | 74 | M | – | – | – | 6 | – | 35 |
| 21 | 68 | M | 9 | – | 8 | – | 7 | 20 |
| 22 | 51 | M | 7 | – | 3 | – | 5 | 8 |
| 23 | 59 | M | 8 | 5 | 4 | 2 | 6 | 10 |
| | 44.3Y | 15/8 | 87%* | 52%* | 74%* | 43%* | 52%* | 10.2 YRS. |

* PERCENTAGE FREQUENCY OF SYMPTOMS IN THE COHORT

FIG. 1

TREATMENT OF NON-INFLAMMATORY AND NON-INFECTIOUS BOWEL DISORDERS

This application is a Continuation of application Ser. No. 08/030,281, filed as PCT/AU91/00482, Oct. 17, 1991, published as WO92/06690, Apr. 30, 1992.

TECHNICAL FIELD

This invention relates to the production and use of therapeutic agents for the treatment of certain bowel disorders, namely disorders arising from unknown or non-obvious causes, which are unaccompanied by inflammation and are not due to detectable infection by known pathogenic organisms. Such disorders are referred to as non-specific bowel disorders hereinafter, and may be distinguished from specific bowel disorders having a diagnosable cause which may be treated by appropriate medication or surgery. Typical non-specific bowel disorders are irritable bowel syndrome (IBS), chronic constipation, non-ulcer dyspepsia (NUD), gastro-oesophageal reflux with or without oesophagitis (GOR), and diverticular disease.

BACKGROUND ART

The human large bowel (colon), and to a lesser extent the small bowel, contain large concentrations of various enteric bacteria. They may range in concentration from between $10^2$ to $10^7$ per cubic centimeter in the small bowel and up to $10^{14}$ per cubic centimeter in the large bowel. When the bacteria are non-pathogenic, then the bowel produces no symptoms in the body.

On the other hand when the normal bowel flora is invaded or joined by pathogenic bacterial strains which may colonise the bowel and remain there long-term, chronic illness can result.

The local effects of abnormal bowel flora may include abdominal cramps caused by colonic or small bowel contraction, distension caused by either fluid or gas accumulation, diarrhoea caused by inadequate fluid absorption or excessive secretion, or constipation by abnormal motility patterns and excessive absorption of water. Severe local effects of abnormal bowel flora can include microscopic or collagenous colitis, ulcerative colitis, Crohn's disease and diverticulosis. Some of these effects are caused by local toxins, others by invasion of bacteria into the bowel lining and in others, the mechanisms are unknown.

When obvious, visible or microscopic colitis is present, it is known that beneficial clinical effects can be obtained from well known anti-bacterial drugs derived from salicylic acid, such as sulfasalazine (prepared by coupling 2-sulfanilamidopyridine with salicylic acid), 4-aminosalicylic acid, 5-aminosalicylic acid, and benzalazine.

When there are no visible abnormalities detectable in the colon and when stool tests, histology and blood tests are negative, yet patients still complain of symptoms referrable to the colon, a diagnosis of IBS will often be made. Some 10–25% of the Western population suffer with this disorder which has also been termed spastic or irritable colon, unstable colon, colonic neurosis, spastic colitis or mucus colitis. In the classic case, there is a triad of symptoms including lower abdominal pain relieved by defecation, alternating constipation and diarrhoea and the passage of small calibre stools. Abdominal distension, flatulence or wind are also frequently present, as is passage of mucus as well as the sensation of incomplete evacuation. All these symptoms are present in the absence of demonstrable organic disease.

The pathogenesis of IBS has hitherto been unknown. Emotional disturbance, fibre deficiency, purgative abuse and food intolerance have all been implicated but not proven nor well demonstrated. Evidence for infection or autoimmunity is lacking. Conventional treatments for IBS have been unsatisfactory, as instanced by the very number of therapies that have, from time to time, been recommended or trialled. These have ranged from psychotherapy and dietary regimes to medication by antispasmodic agents, anticholinergic agents, barbiturates, antidepressants, bulking agents, dopamine antagonists, carminatives, opioids, and tranquillisers; all without signal success. There is no evidence that cure is possible.

IBS is one of the most common of the gastrointestinal illnesses, and though not life-threatening, causes great distress to those severely afflicted and brings a feeling of frustration and helplessness to the physicians attempting to treat it.

DISCLOSURE OF THE INVENTION

The present invention arose from observations by the applicant that treatments of patients for other complaints requiring the administration of antibiotics appeared sometimes to produce beneficial results in respect of IBS and other non-specific bowel disorders. This led to the hypothesis that as yet unproven and undocumented bowel flora alterations or infection by mildly pathogenic bacteria constitutes the mechanism which underlines the pathogenesis of non-specific bowel disorders. Having postulated infection as being the cause of irritable bowel syndrome and the other above-mentioned enteric afflictions, the applicant conducted clinical trials which have shown that antibiotic agents derived from salicylic acid, such as sulfasalazine, 5-aminosalicylic acid compounds, 4-aminosalicylic compounds and benzalazine are capable of suppressing the symptoms in most patients provided the appropriate dose is administered.

The invention consists in a method of treating non-specific bowel disorders comprising the step of dosing a patient suffering therefrom with an antibiotic agent, being a salicylic acid derivative.

According to a second aspect, the invention consists in an antibiotic agent, being a salicylic acid derivative, when used for the treatment of a non-specific bowel disorder.

According to a third aspect the invention consists in the use of a salicylic acid derivative in the manufacture of a medicine for use in the treatment of non-specific bowel disorders.

In preferred embodiments the salicylic acid derivative is one of the group comprising sulfasalazine, the aminosalicylic compounds, including 5-aminosalicylic acid (5-ASA) and 4-aminosalicylic acid (4-ASA), and benzalazine. Furthermore the compound chosen may be related, with advantage, to the particular disorder involved. Specifically, any of the foregoing group may be used in relation to constipation, NUD, GOR or diverticular disease, whereas only the aminosalicylic compounds and benzalazine are appropriate for IBS.

In each case the antibiotic may be used in a manner similar to its use for the treatment of inflammatory bowel disease.

Thus the active ingredient may be incorporated with a pharmaceutically acceptable excipient in tablets or capsules. The capsules or tablets may be taken once at night, twice daily or three or more times daily, in dosages ranging from 200 mg through to 18 grams per day. Sulfasalazine is usually administered in tablet form in a dosage of from 500 mg per day to 18 grams per day in divided doses. 5-ASA or its various recently available new formulations and substitutions may be used in similar doses but starting at 250 mg per day. All the 5-amino salicylic acid agents have to be prepared in such a way that they are released in the distal small bowel. This requires the agent to be furnished with an enteric coating or provided in an enteric coated release capsule. If 5-ASA is released in the upper small bowel and is absorbed to any extent, then it is secreted in the kidney and cuases kidney damage because of crystal formation. Suitably coated or encapsulated products are already available for other purposes, for example those marketed under the names olsalazine, salazopyrin or Mesasal.

As a general rule for long term therapy the dosage will commence at a low level and build up to the desired full amount over a few weeks, and the invention extends to multiple packages of individual dosage units to be taken in sequence to provide such a gradual build up.

From the foregoing it will be appreciated that a completely new use has been discovered for these antibiotics in an area where previously there has been no known effective treatment.

BRIEF DESCRIPTION OF THE DRAWINGS

FIG. 1 is a tabulation of the symptoms and their severity of a group of patients as at the commencement of a clinical trial of the invention.

BEST MODE OF CARRYING OUT THE INVENTION

Figure 2:
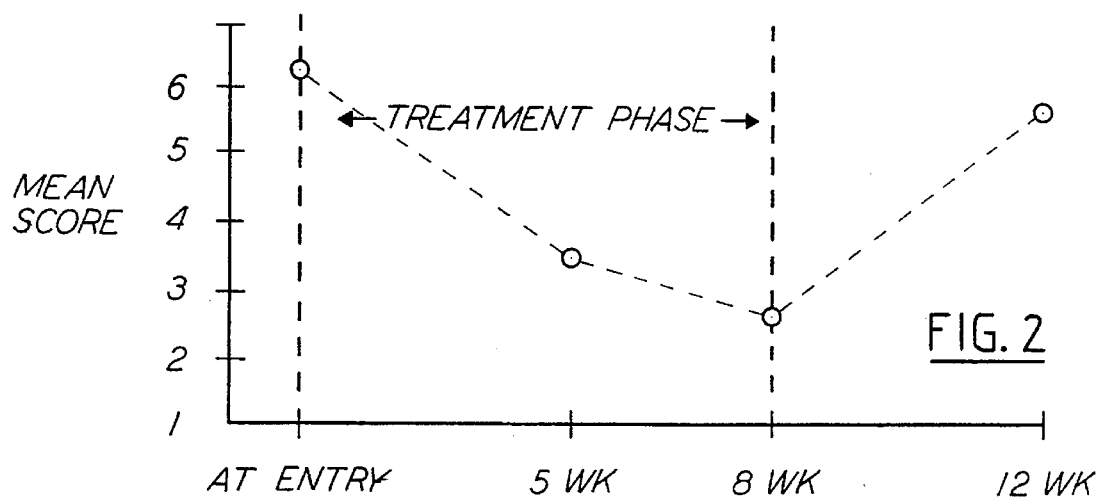
FIGS. 2, 3 and 4 are graphical representations of selected results of the said clinical trial.

The best mode of carrying out the invention known to the applicant may be readily appreciated from the following description of two experimental case studies and subsequent clinical trials prompted by the apparent success of those cases.

INDIVIDUAL CASE STUDIES

EXAMPLE 1

A 31 year old nursing sister (HB) was investigated for chronic abdominal pain and frequent (2–6/day) loose motions with occasional constipation. Stool cultures, large and small biopsy, small bowel enema X-ray, full blood count and multiple biochemical tests revealed no abnormalities. In spite of use of added fibre, food exclusion diets and antispasmodics, the symptoms essentially continued. Introduction of sulfasalazine (Salazopyrin-EN) in a dose of 1 g. b.d. resulted in abolition of pain and reversal of loose motions to formed stools. Withdrawal of therapy brought on recrudescence of original symptoms. Recommencement of sulfasalazine again brought prompt relief. The patient continued to obtain the relief at 5 months follow-up. She was then changed to 5-ASA therapy (utilising the medication marketed as Dipentum) and has been able to continue with the same relief suppression for over a year and a half.

EXAMPLE 2

A 42 year old female sales representative (LA) presented with lower, and occasionally generalised, abdominal cramping together with predominantly loose motions. In spite of extensive gastrointestinal investigations no organic cause was found. Commencement of dosing with sulfasalazine 1 g. b.d. was accompanied by relief of almost all symptoms within 4–5 days. At 3 weeks, however, the patient developed a pronounced rash and treatment was withdrawn. 5-ASA (Dipentum) was not immediately available. Symptoms recurred. When 5-ASA was commenced at a dose of 2 tablets twice daily, the pain and loose motions again abated.

5-ASA has also been used successfully to treat non-ulcer dyspepsia in a number of patients. The dosage commenced at 250 mg per day and is increased to 1 g a day in the usual situation. At weeks 3–6 the effects commence with patients noticing reduction in reflux symptoms and upper GI tract bloating, eructation and burning. Similarly, chronic constipation is controlled by sulfasalazine in doses mentioned above and by the aminosalicylic acid compounds in the majority of patients in the doses described.

CLINICAL TRIAL

Patients and Method

The study was carried out on patients referred by general practitioners to a Medical Centre for Digestive Diseases, for colonoscopic evaluation of abdominal discomfort and bowel disturbances severe enough to warrant further investigation. All patients gave informed consent to take part in the trial, which was conducted in accordance with the Revised Declaration of Helsinki.

Patients with the clinical diagnosis of IBS were offered entry into the trial if their symptom complex satisfied the Manning criteria and complied with the exclusion criteria.

Exclusion criteria were:
i colonoscopic abnormalities eg. visible colitis, polyps, carcinoma or diverticulosis;
ii histological abnormalities eg. collagenous or microscopic colitis;
iii coagulopathy;
iv pregnancy or lactation;
v significant clinical or laboratory evidence of pulmonary, hepatic or renal disease or dysfunction;
vi sensitivity to salicylates; and
vii need for non-steroidal anti-inflammatory drugs, steroids, anti-coagulants or antispasmodic agents.

The study was an open-label, single-institution, unblinded prospective pilot trial aimed at establishing whether a controlled double-blind trial is warranted.

Medication

A 5-ASA formulation, namely olsalazine, (DIPENTUM; KABI-PHARMACIA) was used in the form of 250 mg capsules. To reduce side effects the olsalazine was administered in a stepwise manner from 250 mg b.d. in week 1,500 mg b.d. in week 2, to 750 mg b.d. by week 3 and onwards. The dosage was maintained at 750 mg b.d. for 6 weeks. Those patients unable to tolerate the 750 mg b.d. dose were maintained on the highest dose tolerated.

Symptom Assessment

The severity of symptoms was assessed by the use of a visual analog scale at entry into the trial, at 5 weeks, at termination of trial (8 weeks) and at a 12 week follow-up consultation. The analog scale consisted of a line marked by numbers at equal intervals from 0 to 10. Zero indicated absence of symptoms while 10 represented symptoms severe enough to interfere with work or requiring medication. Assessed symptoms included abdominal pain/discomfort, constipation, diarrhoea, abdominal distension and flatulence. Symptom scores were tabulated and statistical analysis carried out using Students t-test.

Results

Of 26 patients enrolled in the study, data from 23 who completed the entire trial was available for evaluation. One patient terminated the trial prematurely due to excessive headaches, while 2 failed to return at appropriate intervals for symptom follow-up. Included were 8 males and 15 females ranging in age from 24 to 74 years (average=44.3 years). Estimated duration of IBS symptoms ranged from 3 to 35 years, the average being 10.2 years.

Patients' initial characteristics are summarised in FIG. 1. Frequency and severity of the five evaluated symptoms at entry into the trial can be obtained from the listed visual analog scores. Most patients appeared to single out a dominant symptom by assigning higher scores.

Symptom Improvement

In a global assessment of their symptomatology most patients noted improvements in their dominant symptoms. Four patients of the 23 reported no appreciable change in their chief symptoms of pain (2) and constipation (2). The other nineteen patients reported a mean global improvement of 62% at 8 weeks. Abdominal pain, in particular, was significantly reduced. This was so whether the pain was diffuse, lower abdominal, left-iliac-fossa or left or right-upper-quadrant in location. Both diarrhoea and constipation also significantly improved towards normality. Flatulence and bloating symptoms showed lesser, sporadic improvement.

a. ABDOMINAL PAIN: Maximal improvement in pain scores occurred at 8 weeks. The initial score of 6.25 ±1.74 (SD) fell to 2.55 ±1.47 ($p<0.005$). However, by week 12 the score returned to 5.7 ±1.69, being 91% of the pain score at entry.

b. DIARRHOEA: Significant reduction in the diarrhoea score was noted at both the 5 and 8 week consultation. The change in symptom score fell from 6.77 ±1.69 (SD) at entry to 2.35 ±1.08 at 5 weeks and to 2.11 ±0.60 at 8 weeks ($p<0.005$). The score rose to 4.18 ±1.33 by 12 weeks.

c. CONSTIPATION: Significant improvement was also noted in the symptom scores for constipation. Baseline severity score reached its nadir at 8 weeks falling from 6.1 ±1.60 (SD) to 2.3 ±0.48 ($P<0.005$). The score rose again to pre-therapy values—5.9 ±1.99—by the 12th week.

d. BLOATING/FLATULENCE: No significant reduction was found for these two symptoms on an overall assessment. In individual cases, however, occasional marked improvement occurred.

Figure 3:
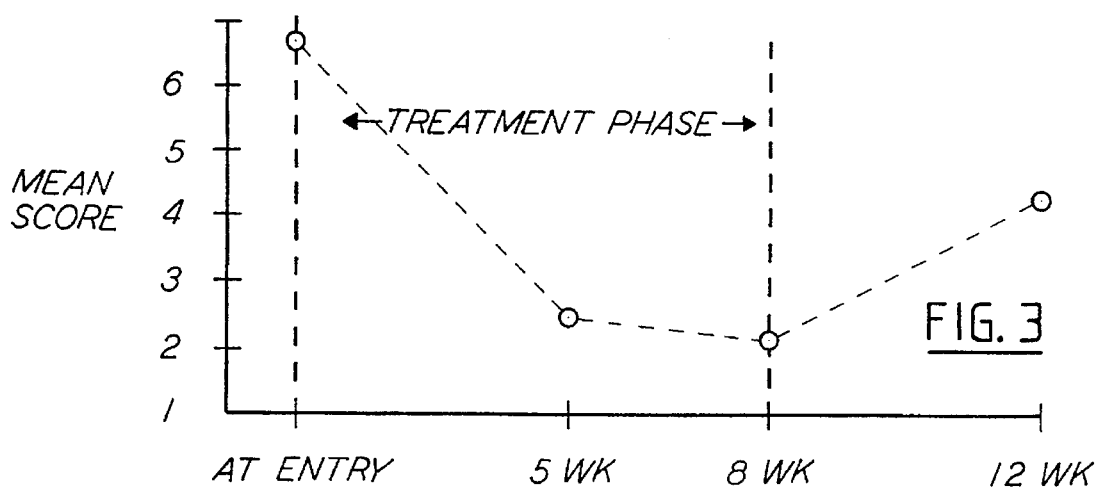
Figure 4:
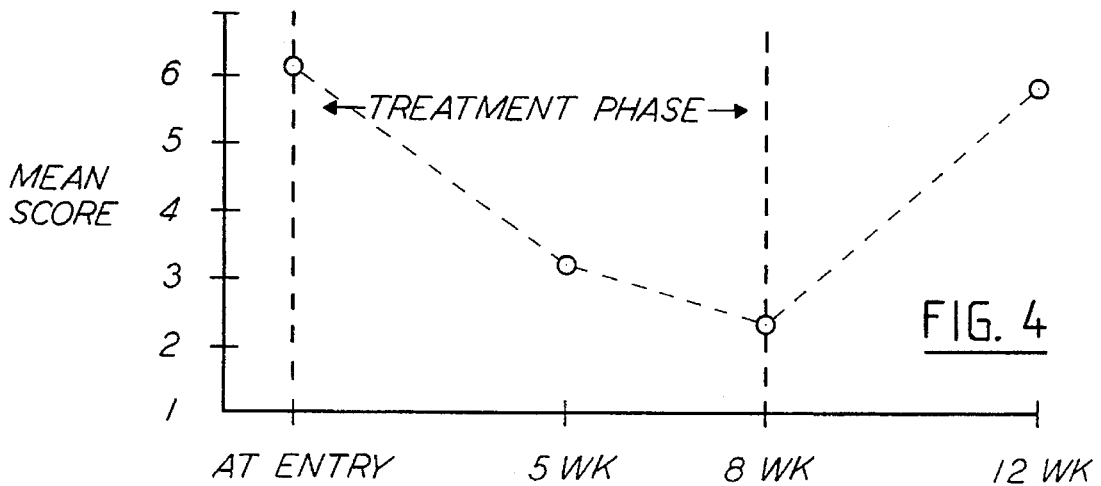

The above described results are shown in graphical form in FIGS. 2, 3 and 4, which represent the symptoms of abdominal pain, diarrhoea and constipation respectively, as assessed at intervals before, during and after treatment with 5-aminosalisylic acid (olsalazine). Not all patients experienced all three symptoms, the number of patients experiencing each symptom being indicated by the number n in each figure.

When asked if they would choose to take the medication on a long term basis 61% of patients expressed the desire to do so. Reasons for not wanting to continue medication included excessive intake of medication (6 capsules per day) or inadequate relief of symptoms for the therapy taken. Several patients specifically indicated that of the numerous therapies tried previously, olsalazine was the first to really improve their symptoms.

Six patients have continued to take olsalazine for between 8 and 21 months for the symptoms of pain, constipation or diarrhoea. Symptom control continued with maintenance therapy. Withdrawal of treatment resulted in recrudescence of symptoms which could again be suppressed by recommencement of olsalazine.

Adverse Effects

Headache and nausea were recorded as the only discernible side effects of this slow, step-wise dose regimen. This occurred in four patients. No allergic reactions occurred. In one patient with constipation loose to normal motions were noted at a dose of 250 mg b.d., at which level the patient was therefore maintained.

I claim:

1. A method of treating non-inflammatory bowel disorders, said method consisting essentially of the step of administering to a patient suffering form said non-inflammatory bowel disorder with from 200 mg to 18 g per day of an anti-inflammatory agent selected from a salicylic acid derivative.

2. A method of treating non-inflammatory bowel disorders, according to claim 1, wherein said anti-inflammatory agent is selected from the group consisting of sulfasalazine, 5-aminosalicylic acid, 4-aminosalicylic acid, benzalazine, and various mixtures thereof.

3. A method of treating non-inflammatory bowel disorders, according to claim 2, wherein a dosage rate administered to said patient commences at a low commencement rate and is escalated over time through at least one larger intermediate rate to a still larger final rate.

4. A method of treating non-inflammatory bowel disorders, according to claim 1, wherein said non-inflammatory bowel disorder is one of constipation, non-ulcer dyspepsia, gastro-oesophageal reflux with oesopagitis, gastro-oesophageal reflux without oesopagitis, and diverticular disease.

5. A method of treating non-inflammatory bowel disorders, according to claim 4, wherein said anti-inflammatory agent is sulfasalazine and a dosage rate administered to said patient is within a range of from 200 mg to 18 g per day.

6. A method of treating non-inflammatory bowel disorders, according to claim 5 wherein a dosage rate administered to said patient commences at a low commencement rate and is escalated over time through at least one larger intermediate rate to a still larger final rate.

7. A method of treating non-inflammatory bowel disorders, according to claim 4, wherein a dosage rate administered to said patient commences at a low commencement rate and is escalated over time through at least one larger intermediate rate to a still larger final rate.

8. A method of treating non-inflammatory bowel disorders, according to claim 1, wherein said non-inflammatory bowel disorder is irritable bowel syndrome.

9. A method of treating non-inflammatory bowel disorders, according to claim 8, wherein said anti-inflammatory agent is selected from the group consisting of 5-aminosalicylic acid, 4-aminosalicylic acid, benzalazine, and various mixtures thereof and a dosage rate administered to said patient is within a range of from 250 mg to 10 g per day.

10. A method of treating non-inflammatory bowel disorders, according to claim 8, wherein a dosage rate administered to said patient commences at a low commencement rate and is escalated over time through at least one larger intermediate rate to a still larger final rate.

11. A method of treating non-inflammatory bowel disorders, according to claim 8, wherein a dosage rate administered to said patient commences at a low commencement rate and is escalated over time through at least one larger intermediate rate to a still larger final rate.

12. A method of treating non-inflammatory bowel disorders, according to claim 9 wherein a dosage rate administered to said patient commences at a low commencement rate and is escalated over time through at least one larger intermediate rate to a still larger final rate.

* * * * *